(12) United States Patent
Goswami et al.

(10) Patent No.: US 11,920,828 B2
(45) Date of Patent: Mar. 5, 2024

(54) SYSTEM AND METHOD FOR PHOTOELECTROCHEMICAL AIR PURIFICATION

(71) Applicant: Molekule Inc., San Francisco, CA (US)

(72) Inventors: Dilip N. Goswami, San Francisco, CA (US); Philip Myers, San Francisco, CA (US)

(73) Assignee: Molekule, Inc., San Francisco, CA (US)

( * ) Notice: Subject to any disclaimer, the term of this patent is extended or adjusted under 35 U.S.C. 154(b) by 15 days.

(21) Appl. No.: 16/831,354

(22) Filed: Mar. 26, 2020

(65) Prior Publication Data

US 2020/0222576 A1     Jul. 16, 2020

Related U.S. Application Data

(63) Continuation of application No. PCT/US2018/056061, filed on Oct. 16, 2018.
(Continued)

(51) Int. Cl.
| | | |
|---|---|---|
| *A61L 9/20* | (2006.01) | |
| *A61L 9/22* | (2006.01) | |
| *B01J 21/06* | (2006.01) | |
| *B01J 35/00* | (2006.01) | |
| *B01J 35/02* | (2006.01) | |

(Continued)

(52) U.S. Cl.
CPC .............. *F24F 8/192* (2021.01); *A61L 9/205* (2013.01); *A61L 9/22* (2013.01); *B01J 21/063* (2013.01); *B01J 35/004* (2013.01); *B01J 35/023* (2013.01); *F24F 8/10* (2021.01); *F24F 8/167* (2021.01); *A61L 2209/14* (2013.01); *A61L 2209/15* (2013.01); *A61L 2209/21* (2013.01); *B01J 21/185* (2013.01); *B01J 2208/026* (2013.01);
(Continued)

(58) Field of Classification Search
CPC ........ A61L 9/205; A61L 9/22; A61L 2209/14; A61L 2209/15; A61L 2209/21; A01J 35/004; A01J 35/023; B82Y 40/00
See application file for complete search history.

(56) References Cited

U.S. PATENT DOCUMENTS

| | | |
|---|---|---|
| 2,311,272 A | 2/1943 | Ware |
| 4,065,276 A | 12/1977 | Nakaya et al. |

(Continued)

FOREIGN PATENT DOCUMENTS

| | | |
|---|---|---|
| CN | 107096320 A | 8/2017 |
| CN | 107344043 A | 11/2017 |

(Continued)

OTHER PUBLICATIONS

InternationalSearch Report and Written Opinion for application No. PCT/US21/16464 dated Jul. 1, 2021.
(Continued)

*Primary Examiner* — Timothy C Cleveland
(74) *Attorney, Agent, or Firm* — Jeffrey Schox; Randy Mehlenbacher

(57) ABSTRACT

An air purification system including a filter assembly including a substrate including a fibrous media, and a photocatalytic material disposed on the substrate, wherein the photocatalytic material includes a first quantity of crushed nanostructures; and a photon source arranged to illuminate the photocatalytic material with optical radiation.

12 Claims, 7 Drawing Sheets

Related U.S. Application Data

(60) Provisional application No. 62/573,624, filed on Oct. 17, 2017.

(51) Int. Cl.
*F24F 8/10* (2021.01)
*F24F 8/167* (2021.01)
*F24F 8/192* (2021.01)
B01J 21/18 (2006.01)
B82Y 40/00 (2011.01)
F24F 8/22 (2021.01)

(52) U.S. Cl.
CPC .......... B01J 2219/248 (2013.01); B82Y 40/00 (2013.01); F24F 8/22 (2021.01)

(56) References Cited

U.S. PATENT DOCUMENTS

| | | | |
|---|---|---|---|
| 4,896,590 A | 1/1990 | Groos | |
| 4,931,654 A | 6/1990 | Horng | |
| D328,946 S | 8/1992 | Havrilla | |
| 5,240,479 A | 8/1993 | Bachinski | |
| D360,635 S | 7/1995 | Mark | |
| D362,441 S | 9/1995 | Mark | |
| 5,505,904 A | 4/1996 | Haidinger et al. | |
| 5,620,669 A | 4/1997 | Plinke et al. | |
| 5,709,735 A | 1/1998 | Midkiff et al. | |
| D400,663 S | 11/1998 | Furlough | |
| 5,922,093 A | 7/1999 | James et al. | |
| 6,372,694 B1 | 4/2002 | Osinga et al. | |
| 6,531,100 B1 | 3/2003 | Ogata et al. | |
| 6,607,702 B1 | 8/2003 | Kang et al. | |
| D493,874 S | 8/2004 | Woods | |
| D505,999 S | 6/2005 | Song | |
| D552,724 S | 10/2007 | Chen | |
| D611,579 S | 3/2010 | Zlotnik et al. | |
| 7,786,033 B2 | 8/2010 | Marzolin et al. | |
| D648,429 S | 11/2011 | Choi et al. | |
| 8,048,391 B2 | 11/2011 | Molins | |
| D652,408 S | 1/2012 | Chen | |
| D687,017 S | 7/2013 | Ashcraft et al. | |
| D697,496 S | 1/2014 | Ashcraft et al. | |
| 8,658,046 B2 | 2/2014 | Barry et al. | |
| 8,691,144 B2 | 4/2014 | Garfield et al. | |
| D710,329 S | 8/2014 | Holzer | |
| D716,427 S | 10/2014 | Lim et al. | |
| D717,420 S | 11/2014 | Von Seggern | |
| 8,951,376 B2 | 2/2015 | Rasmussen | |
| D744,541 S | 12/2015 | Langhammer et al. | |
| D752,732 S | 3/2016 | Ansley et al. | |
| D754,832 S | 4/2016 | Seo et al. | |
| D766,213 S | 9/2016 | Hinokio | |
| D768,844 S | 10/2016 | Koseoglu et al. | |
| D773,704 S | 12/2016 | Pardo et al. | |
| D774,020 S | 12/2016 | Hinokio | |
| D796,019 S | 8/2017 | Thompson | |
| D802,022 S | 11/2017 | Yao et al. | |
| D803,369 S | 11/2017 | Kim et al. | |
| D803,810 S | 11/2017 | Lee et al. | |
| D804,002 S | 11/2017 | Huang | |
| D805,622 S | 12/2017 | Lee | |
| D806,843 S | 1/2018 | McDonnell | |
| D807,327 S | 1/2018 | Xiong | |
| D808,927 S | 1/2018 | Schaal et al. | |
| D810,049 S | 2/2018 | Lee et al. | |
| D810,135 S | 2/2018 | Langhammer et al. | |
| D810,137 S | 2/2018 | Tsang et al. | |
| D810,265 S | 2/2018 | Chen | |
| D810,266 S | 2/2018 | Li | |
| D818,097 S | 5/2018 | Cho et al. | |
| D828,912 S | 9/2018 | Powell et al. | |
| D829,312 S | 9/2018 | Riering-Czekalla et al. | |
| D829,313 S | 9/2018 | Cho et al. | |
| D829,314 S | 9/2018 | Cho et al. | |
| D831,810 S | 10/2018 | Cho et al. | |
| D831,811 S | 10/2018 | Cho et al. | |
| D832,414 S | 10/2018 | Sharma et al. | |
| D834,694 S | 11/2018 | Walter et al. | |
| 10,137,216 B2 | 11/2018 | Goswami et al. | |
| D835,766 S | 12/2018 | Chen | |
| D836,760 S | 12/2018 | Fredäng et al. | |
| 10,183,187 B2 | 1/2019 | Li | |
| D850,596 S | 6/2019 | Wu | |
| D865,149 S | 10/2019 | Lin | |
| D865,932 S | 11/2019 | Ha et al. | |
| D870,870 S | 12/2019 | Copparstad et al. | |
| 10,549,268 B2 | 2/2020 | Ozaki et al. | |
| D879,276 S | 3/2020 | King | |
| D884,138 S | 5/2020 | Chen | |
| D884,860 S | 5/2020 | Zhang | |
| D886,268 S | 6/2020 | Montagnino et al. | |
| D886,272 S | 6/2020 | Yang et al. | |
| 2002/0160913 A1 | 10/2002 | Sangiovanni et al. | |
| 2003/0180200 A1 | 9/2003 | Reisfeld | |
| 2004/0013583 A1 | 1/2004 | Burkhardt | |
| 2004/0166037 A1 | 8/2004 | Youdell et al. | |
| 2004/0262217 A1 | 12/2004 | Mori et al. | |
| 2005/0061656 A1 | 3/2005 | Benoit et al. | |
| 2005/0132682 A1 | 6/2005 | Paul | |
| 2005/0138905 A1 | 6/2005 | Kubokawa | |
| 2005/0193696 A1 | 9/2005 | Muller et al. | |
| 2006/0150818 A1 | 7/2006 | Okamoto et al. | |
| 2007/0199288 A1 | 8/2007 | Paterson et al. | |
| 2007/0289270 A1 | 12/2007 | Schumann et al. | |
| 2007/0296035 A1 | 12/2007 | George et al. | |
| 2008/0112845 A1 | 5/2008 | Dunn et al. | |
| 2009/0002985 A1 | 1/2009 | Peck et al. | |
| 2009/0010801 A1 | 1/2009 | Murphy et al. | |
| 2009/0175757 A1 | 7/2009 | Yao et al. | |
| 2009/0229478 A1 | 9/2009 | Wu | |
| 2009/0245594 A1 | 10/2009 | Abramovich et al. | |
| 2010/0101413 A1 | 4/2010 | Jones et al. | |
| 2010/0143205 A1 | 6/2010 | Engelhard | |
| 2010/0196223 A1 | 8/2010 | Hay et al. | |
| 2010/0260644 A1 | 10/2010 | Day et al. | |
| 2011/0101712 A1 | 5/2011 | Laconte | |
| 2011/0117002 A1 | 5/2011 | Dardas et al. | |
| 2012/0077668 A1 | 3/2012 | Takada et al. | |
| 2012/0161405 A1 | 6/2012 | Mohn et al. | |
| 2012/0301363 A1 | 11/2012 | Kim et al. | |
| 2013/0036908 A1 | 2/2013 | Jones et al. | |
| 2014/0131923 A1 | 5/2014 | Festner et al. | |
| 2014/0271419 A1 | 9/2014 | Tsotsis et al. | |
| 2014/0290489 A1 | 10/2014 | Uemura et al. | |
| 2015/0008014 A1 | 1/2015 | Zhou et al. | |
| 2015/0320900 A1 | 11/2015 | Goswami et al. | |
| 2016/0129432 A1* | 5/2016 | Ozaki | A61L 9/205 502/309 |
| 2016/0367916 A1 | 12/2016 | Koehler | |
| 2017/0043044 A1 | 2/2017 | Sobhy | |
| 2017/0122605 A1 | 5/2017 | Lee et al. | |
| 2017/0321717 A1 | 11/2017 | Park et al. | |
| 2018/0001312 A1 | 1/2018 | Shibai et al. | |
| 2018/0027809 A1 | 2/2018 | Chiattello et al. | |
| 2018/0117511 A1 | 5/2018 | Yamauchi et al. | |
| 2018/0221856 A1 | 8/2018 | Li et al. | |
| 2019/0314751 A1 | 10/2019 | Cheng et al. | |
| 2020/0061635 A1 | 2/2020 | Wiser et al. | |
| 2020/0109869 A1 | 4/2020 | Mäkipää et al. | |

FOREIGN PATENT DOCUMENTS

| | | |
|---|---|---|
| JP | H0668820 U | 9/1994 |
| JP | H11505746 A | 5/1999 |
| JP | 2001025668 A | 1/2001 |
| JP | 2001232154 A | 8/2001 |
| JP | 2002263175 A | 9/2002 |
| JP | 2002291856 A | 10/2002 |
| JP | 2003062414 A | 3/2003 |
| JP | 2003070885 A | 3/2003 |
| JP | 2007190533 A | 8/2007 |
| JP | 2008522822 A | 7/2008 |
| JP | 2016530908 A | 10/2016 |

(56) References Cited

FOREIGN PATENT DOCUMENTS

| JP | 2017148484 A | 8/2017 |
|---|---|---|
| KR | 19990021845 A | 3/1999 |
| WO | 9637281 A1 | 11/1996 |
| WO | 2004078320 A1 | 9/2004 |
| WO | 2006065491 A2 | 6/2006 |
| WO | 2015002324 A1 | 1/2015 |
| WO | 2015098386 A1 | 7/2015 |

OTHER PUBLICATIONS

Molekule Air Purifier found online—[Feb. 22, 2018]—https://molekule.com/?utm_source=google_search_search&utm_medium=rt&utm_campaign=brand&utm_term=term=molekule&utm_content-bmm_2&gclid=EAalQobChMI5ufdtbK62QIViYjlCh3d8gvEAYAASAAEgJcdPD_BwE.

Hou, et al. "A review of surface plasmon resonance-enhanced photocatalysis" Advanced 4, 15 Functional Materials 23.13 (Apr. 5, 2013): 1612-1619. p. 1 col. 2 para 1, p. 2 col. 1 para 2.

International Search report and Written Opinion for PCT Application No. PCT/US19/43804 dated Dec. 2, 2019.

Molekule Website Screen Capture from Jun. 10, 2016 by Wayback Machine, (Year: 2016).

Ochiai, et al. "Photoelectrochemical properties of TiO2 photocatalyst and its applications for environmental purification." Journal of Photochemistry and Photobiology C: Photochemistry reviews 13.4 (Dec. 1, 2012): 247-262.

Darlrymple, Omatoyo K., et al., "A review of the mechanisms and modeling of photocatalytic disninfection", Applied Catalysis B.: Environmental 98 (2010) 27-38.

Larzelere, John, "New and Novel Technologies in Particulate Filtration", https://apps.dtic.mil/sti/pdfs/ADA444770.pdf, 2006.

Marzocchi, Alfred, et al., "Glass Fibers and Their Use as Filter Media", Journal of the Air Pollution Association, Mar. 19, 2012.

Neves, Ana I.S., et al., "Towards conductive textiles: coating polymeric fibers with graphene", Nature, Scientific Reports 7: 4250, Mar. 7, 2017.

Wertz, John, et al., "Filtration media: Advantages of nanofibre coating technology", Filtration Seperation, Sep. 7, 2009.

"Water-Based Adhesives-Information and Overview", https://www.hotmelt.com/blogs/blog/water-based-adhesives-information-and-overview.

Evans, Hugh, "Adhesives: Understanding adhesives for filter fabrication", Filter Media Apr. 26, 2012, https://www.filtsep.com/filter%20media/features/adhesives-understanding-adhesives-for-filter/.

Merrill, Reynold C., et al., "Chemistry of the soluble silicates", J. Chem. Educ. 1947, 24, 6, 262, Jun. 1, 1947, https://pubs.acs.org/doi/pdf/10.1021/ed024p262.

Cao, Jinshan, et al., "Patterned nanofiber air filters with high optical transparency, robust mechanical strength, and effective PM2.5 capture capability", RSC Adv., 2020, 10, 20155.

Henning, Laura M., et al., "Review on Polymeric, Inorganic, and Composite Materials for Air Filters: From Processing to Properties", DOI: 10.1002/aesr.202100005 Adv. Energy Sustainability Res. 2021, 2, 2100005.

Liu, Chong, et al., "Transparent air filter for high-efficiency PM2.5 capture", Nature Communications, 6:6205, DOI: 10.1038/ncomms7205, published Feb. 16, 2015.

\* cited by examiner

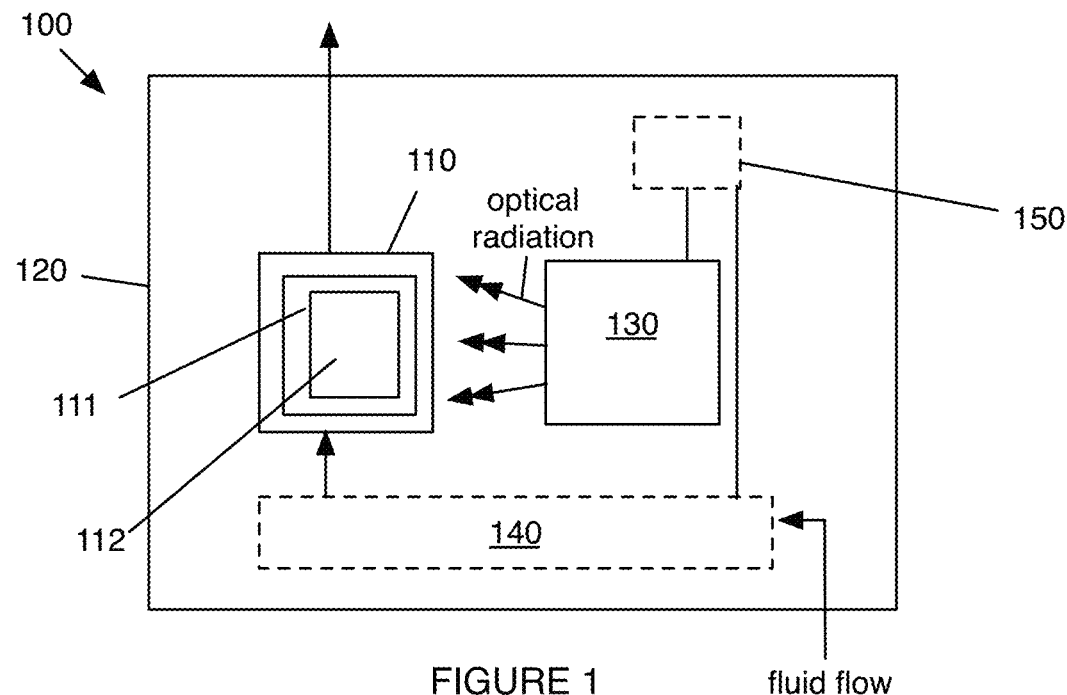
FIGURE 1
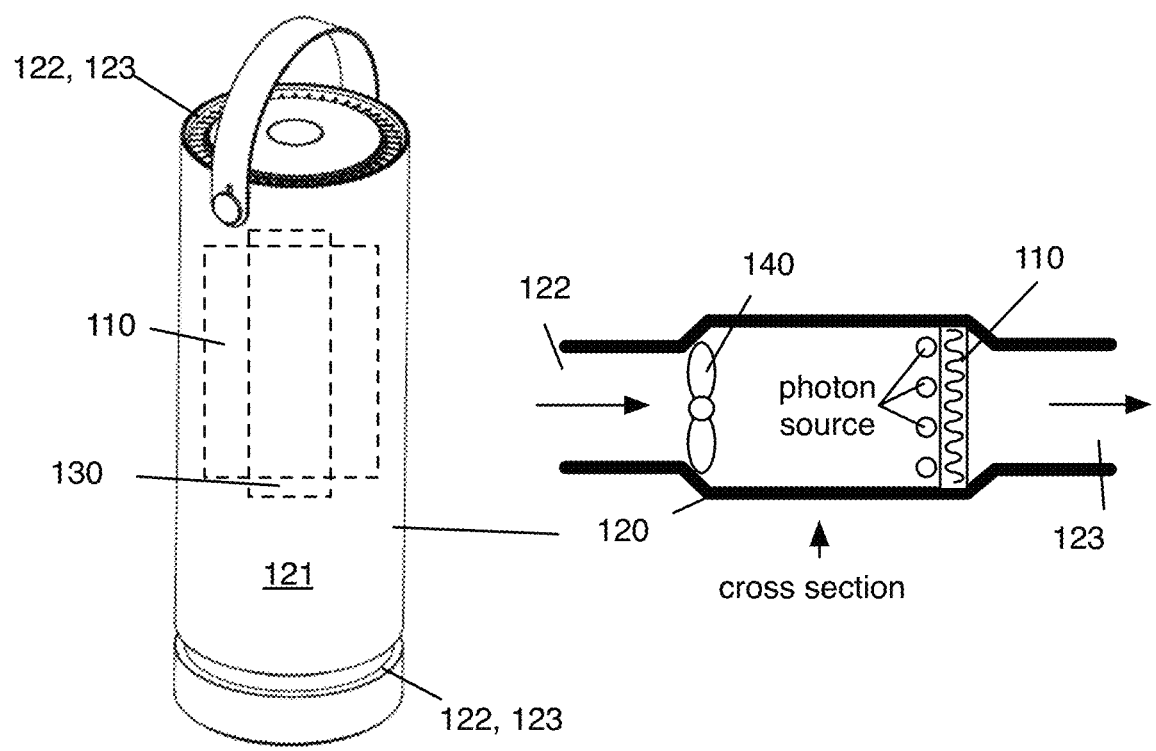
FIGURE 2A
FIGURE 2B

SYSTEM AND METHOD FOR PHOTOELECTROCHEMICAL AIR PURIFICATION

GOVERNMENT LICENSE RIGHTS

This invention was made with government support under contract number EP-D-15-027 awarded by the United States Environmental Protection Agency. The government has certain rights in the invention.

CROSS-REFERENCE TO RELATED APPLICATIONS

This application claims priority to PCT Application No. PCT/US18/56061, filed 16 Oct. 2018 which is incorporated herein in its entirety by this reference.

TECHNICAL FIELD

This invention relates generally to the air purification field, and more specifically to a new and useful system and method for photoelectrochemical air purification in the air purification field.

BACKGROUND

Various filtration systems can be used to reduce the concentration of pollutants in the air. Trapping filters can have low costs, but simply retain pollutants on a filter medium and can thus be fouled by high pollutant concentrations and/or as a result of extended runtimes. In addition, trapping filters can provide a growth medium for biological contaminants, and thus can have a negative effect on air quality. UV disinfection can be employed for biological contaminant elimination but can cause the formation of additional pollutions (e.g., ozone) and is often generally ineffective in degrading many other toxic chemicals such as formaldehyde, styrene, toluene, and other chemicals which are often found in various environments to which humans can be exposed.

Thus, there is a need in the air purification field for a new and useful system for photoelectrochemical air purification. This invention provides such a new and useful system and method of manufacture therefor.

BRIEF DESCRIPTION OF THE FIGURES

FIG. 1 depicts a schematic of an example embodiment of the air purification system;

FIGS. 2A and 2B depict example embodiments of a first example form factor and a second example form factor, respectively, of an example embodiment of the air purification system;

DESCRIPTION OF THE PREFERRED EMBODIMENTS

Figure 3A:
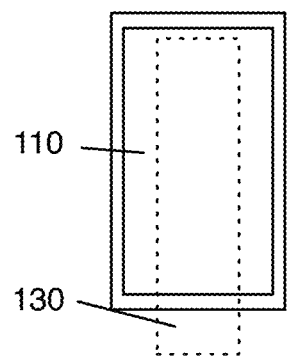
FIGS. 3A and 3B depict example relative arrangements of the filter assembly and the photon source of an example embodiment of the air purification system.

The following description of preferred embodiments of the invention is not intended to limit the invention to these preferred embodiments, but rather to enable any person skilled in the art to make and use this invention.

1. Overview

As shown in FIG. 1, the system 100 includes a filter assembly 110 that includes a substrate 111 and a photocatalytic material 112 disposed on the substrate 111. The system 100 can optionally include: a housing 120 that retains the filter assembly 110, and a photon source 130 (e.g., retained by the housing 120, external to the system 100, etc.) that illuminates the photocatalytic material 112. The system 100 can optionally include a flow control mechanism 140, a controller 150, and any other suitable mechanisms and/or components for facilitating air purification and/or filtration.

The system 100 functions to eliminate airborne pollutants from a fluid stream. Pollutants can include volatile organic compounds (VOCs), biological contaminants (e.g., bacteria, viruses, mold spores, etc.), soot particles, and any other pollutants that can be found in indoor and/or outdoor airflows. The system 100 can also function to integrate into existing airflow systems (e.g., HVAC ducting, vehicle ventilation systems, etc.) and provide such airflow systems with air purification capacity. The system 100 can also function to provide stand-alone purification capacity for indoor and/or enclosed spaces (e.g., as a free-standing air purifier for a domicile or other indoor space, a portable air purifier for a vehicle or temporary shelter, etc.). The system 100 can also function to provide a high surface area photocatalytic surface (e.g., to increase pollutant reduction efficiency). The system 100 can also function to provide a photocatalytic surface that encourages increased localization time periods of pollutants proximal to the surface (e.g., enhances chemical affinity for VOCs and/or other pollutants), increased adsorption rates of pollutants at the surface, an increase in active surface area over the substrate in the absence of photocatalytic material, and any other suitable surface properties related to air purification. However, the system 100 can additionally or alternatively have any other suitable function.

The system 100 can be constructed in various form factors. In a first variation, an example of which is shown in FIG. 2A, the system 100 can be integrated into a standalone air purification module operable to process the air volume of an indoor space (e.g., a bedroom, an office, a warehouse, etc.) over a period of time. In a second variation, an example of which is shown in FIG. 2B, the system 100 can be integrated into an insertable air purification module that can be inserted into a preexisting airflow apparatus (e.g., a ventilation duct, an HVAC system, a central air conditioning system, etc.). However, the system 100 can additionally or alternatively have any other suitable form-factor and can be otherwise suitably configured as a self-contained and/or modular system for air purification.

In variations, the system 100 can receive power from an external source. In the first variation of the system 100, the system 100 can be connected to a source of electrical power (e.g., the power grid) by way of a direct electrical connection (e.g., a power cable). In the second variation of the system 100, the system 100 can convert input power into electrical power (e.g., from an air-driven generator in-line with an integrated ventilation system having a directed airflow), and/or can be connected to a source of electrical power (e.g., the power grid, building power, etc.) by way of a direct electrical connection. In additional or alternative variations, the system 100 can operate substantially passively (e.g., wherein the photon source includes ambient light, sunlight, etc., and the photocatalytic material is utilized as an external coating) and can omit a power source. However, the system 100 can be otherwise suitably powered or unpowered.

The system is preferably manufactured at least in part in accordance with a method of manufacture 200. The method 200 preferably includes: forming a plurality of nanostructures composed at least partially of a photocatalytic compound S210; crushing the plurality of nanostructures to form crushed nanostructures S220; forming a plurality of nanoparticles, at least one of the plurality of nanoparticles including the photocatalytic compound S230; combining the crushed nanotubes and the nanoparticles into a photocatalytic material S240; and attaching the photocatalytic material to a substrate S250.

The method of manufacturing 200 can optionally include: assembling the substrate into a filter assembly, wherein the filter assembly is configured to integrate into an air purification system S260; and any other suitable Blocks or subprocesses related to the manufacture of air purification systems that include crushed nanostructures as an active element.

2. Benefits

Variants of the technology can confer several benefits and/or advantages.

First, variants of the technology can enable air disinfection and purification by destroying (e.g., chemically reducing, oxidizing, eliminating) pollutants (e.g., instead of trapping pollutants fully-constituted and retaining pollutants in chemically identical form). Air purification can be performed via direct oxidation, wherein electron-hole pairs created in the photocatalytic material upon illumination by a photon source create chemically reactive radicals to convert pollutants into constituent, non-harmful (or less harmful) components. Air purification can additionally or alternatively be performed indirectly, wherein electron-hole pairs react with components of the air (e.g., water vapor) to form chemically reactive radicals (e.g., hydroxyl radicals) that, in turn, reduce pollutants in the air into constituent components.

Second, variants of the technology can enable indoor air purification via either an integratable (e.g., into an existing ventilation system) or standalone (e.g., free-standing, modular, portable, etc.) air purifier. Such variants enable flexibility in implementation of the photocatalytic process in various environments.

Third, variants of the technology can enable improvement to the performance of photocatalytic electrochemical oxidation (PECO) systems through the use of crushed photocatalytic nanostructures. Nanostructures can be solid (e.g., rods, nanorods, nanowires, etc.) and/or hollow (e.g. tubes, nanotubes, etc.). Crushed photocatalytic nanostructures can have enhanced surface morphologies, physical and surface chemistry, plasmonic and photonic structures and other reactive characteristics compared to other photocatalytic nanostructures (e.g., nanospheres, nanobeads, nanoparticles, sheets, etc.). The utilization of crushed nanotubes can thus improve reduction efficiency of pollutants. The inclusion of crushed nanotubes into the photocatalytic material can improve pollutant destruction efficiency by, for example, 30% per unit volume of processed airflow, and/or any other suitable efficiency improvement (e.g., 10-100%, 15-200%, etc.).

Fourth, variants of the technology can enable single-pass air purification; for example, variants of the system and/or method can include destruction of pollutants above a threshold percentage reduction (e.g., 80%, 90%, 99.99%, etc.) after a single pass of air flow through the air purification system. Related variants can enable air purification in fewer cycles (e.g., single-pass, double-pass, a smaller number of discrete passes, etc.) than systems that do not employ PECO techniques.

Fifth, variants of the technology can enable pollutant reduction without using ionizing radiation or undesirably high-energy electromagnetic radiation (e.g., UVC, optical radiation having a wavelength shorter than or equal to 280 nm, in the range 100-280 nm, etc.), instead using non-ionizing radiation or lower-energy electromagnetic radiation (e.g., near-IR, near-UV, UV A or optical radiation having a wavelength between 315 and 400 nm, UV B or optical radiation having a wavelength between 280 and 315 nm, visible radiation, any suitable combination of the aforementioned, etc. etc.) to activate the photocatalytic material (e.g., induce formation of electron-hole pairs in the photocatalytic material, excite electrons from the valence band into the conduction band of the photocatalytic material, etc.). By avoiding the use of undesirably high-energy electromagnetic radiation, such variants enhance human safety of the system and reduce the health risks from electromagnetic radiation exposure related to the system.

However, variants of the systems and/or method can confer any other suitable benefits and/or advantages.

3. System

3.1 Housing

The system 100 preferably includes a housing 120. The housing 120 functions to retain the components of the system 100. The housing 120 can also function to define air flow path(s) through the system 100 (e.g., between one or more inlets and one or more outlets). The housing 120 can, in variations, define a housing lumen 121, one or more inlets 122, and one or more outlets 123 as shown in FIGS. 2A-2B. The housing 120 can be a single unitary body but can additionally or alternatively include a plurality of interlocking housing sections defining a body, a free-standing support, and/or any other suitable housing sections or components.

The housing 120 preferably defines a substantially complete enclosure but can additionally or alternatively define an open structure (e.g., a rim) and/or any other suitable structure at which system components are retained.

The housing 120 is preferably made of a plastic material (e.g., thermoplastic, polycarbonate, nylon, high- and/or low-density polyethylene, polystyrene, polyurethanes, polyvinyl chloride, acrylonitrile butadiene styrene, etc.), but can additionally or alternatively be made of aluminum (e.g., brushed aluminum, anodized aluminum, etc.), other metallic and/or insulating materials, and/or any other suitable material or combination thereof.

The housing 120 preferably defines a housing lumen 121, through which air flows between an inlet 122 and an outlet 123. The housing lumen functions to define one or more flow pathways between the inlet and the outlet. The housing lumen also functions to retain the filter assembly 110 (e.g., within a volume occupied by air to be purified during use). The housing lumen can define any suitable retention points (e.g., posts, clips, brackets, etc.) at which the filter assembly 110 is retained (e.g., at a filter retention region). However, the housing lumen can be otherwise suitably defined by the housing 120.

In a specific example, the lumen of the housing is open (e.g., not enclosed), and the housing defines one or more structural and/or mechanical interfaces arranged to receive mating components of a ventilation system (e.g., mating surfaces of a ventilation duct of any suitable cross-sectional shape, orifices adapted to couple to the interfaces by way of flexible or substantially flexible tubing or hose, etc.).

The inlet of the housing 120 functions to provide an intake of air (e.g., pollutant-laden air) for provision to the filter assembly 110 and subsequent decontamination. In a first variation of the housing 120, the inlet includes an annular orifice at the base of the housing 120 through which air is drawn into the housing lumen. In a second variation of the housing 120, the inlet includes a broad rectangular opening configured to mate to an existing ventilation system (e.g., by way of a mating interface). However, the inlet of the housing 120 can be otherwise suitably configured.

The outlet of the housing 120 functions to output purified and/or disinfected air from the housing lumen into the ambient environment surrounding the system 100. In a first variation of the housing 120, the outlet includes a set of ports arranged at the top surface of the housing 120.

However, in various examples and/or variations, the system 100 can omit a housing, and/or include any other suitable housing configuration.

3.2 Filter Assembly

The filter assembly 110 functions to provide an activatable surface (e.g., a photocatalytic surface) that, when illuminated by the photon source 130, reduces pollutants in a fluid stream (e.g., air stream) in contact therewith (e.g., urged by a flow control mechanism, urged by an external air flow such as wind, stagnant air in an enclosed or open space, etc.). The filter assembly 110 includes a substrate 111 and a photocatalytic material 112 disposed on the substrate 111. The filter assembly 110 can also include a support structure 113 (e.g., a conductive support structure) in contact with the substrate, and in variations can additionally or alternatively include any suitable support components for retention of the substrate or other suitable components.

Figure 13:
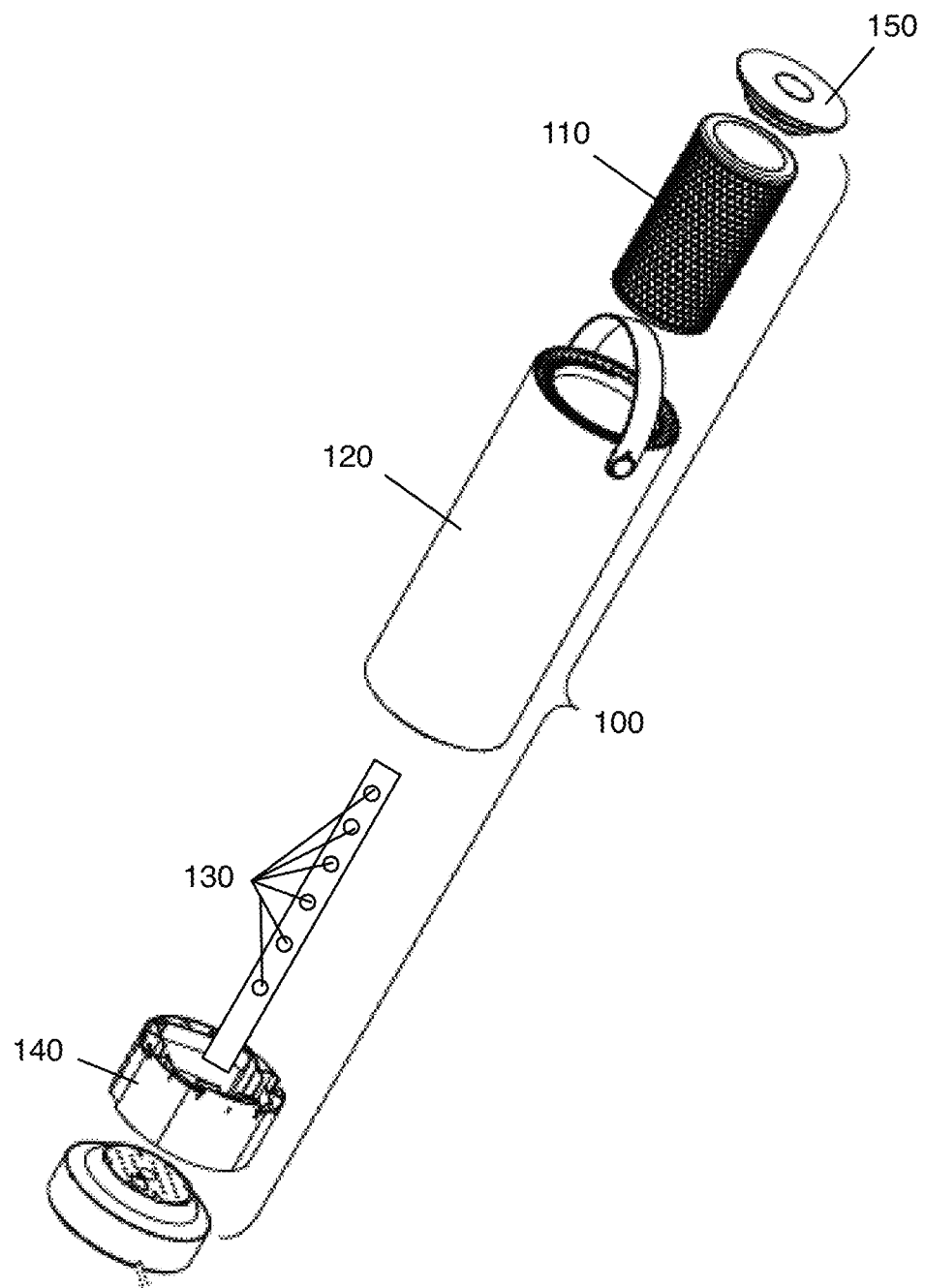
FIG. 13 depicts an exploded view of an example embodiment of the air purification system.

The filter assembly 110 is preferably retained within the housing lumen of the housing 120 (e.g., at a retention region). In a first variation, the filter assembly 110 is arranged concentrically within the housing lumen (e.g., a cylindrical housing lumen as shown by example in FIG. 13).

The filter assembly 110 is preferably in fluid communication with the ambient environment, by way of the inlet and outlet defined by the housing 120. However, the filter assembly 110 can be otherwise suitably fluidly connected (e.g., wherein the filter assembly 110 is arranged within a substantially open lumen and thus open to the air). The filter assembly 110 is preferably arranged proximal the photon source 130, such that the photon source 130 can illuminate at least a portion of the surface area (e.g., the entire surface area, the entirety of one side of the substrate, substantial portions of the surface area of at least one side of the substrate, etc.) of the filter assembly 110 and/or portions thereof (e.g., the substrate on which the photocatalytic material is disposed).

Figure 3B:
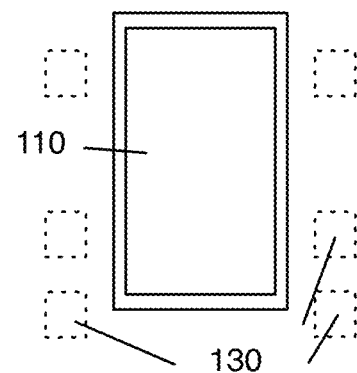

In a first example, the filter assembly 110 is arranged concentrically about the photon source 130 (e.g., in a cylindrical prism circumscribing the photon source) as shown in FIG. 3A. In a second example, the filter assembly 110 is arranged offset from the photon source 130, wherein the photon source 130 is distributed proximal the filter assembly 110 as shown in FIG. 3B. However, the filter assembly 110 can be concentrically arranged within the photon source 130, be arranged parallel the photon source 130, or be otherwise suitably arranged.

The substrate 111 of the filter assembly 110 functions to provide a material to which photocatalytic material 112 can be attached, and with which fluid can be brought into contact (e.g., for purification, for filtration, for pollutant reduction, etc.). The substrate 111 can also function to provide structural support to the photocatalytic material and enable the photocatalytic material to be distributed as desired within the filter assembly 110 and the system 100 as a whole; for example, a substrate can be formed into a corrugated (e.g., pleated) cylindrical shape to enable the photocatalytic material disposed thereupon to be formed into such a shape.

The substrate 111 is preferably directly connected and permanently attached to the filter assembly 110 but can additionally or alternatively be removably coupled to the filter assembly 110. The substrate 111 is preferably connected to the filter assembly by way of a flexible metallic mesh, which together cooperatively form a portion of the filter assembly, wherein the flexible metallic mesh (or other suitable connecting structure) can be bonded to the substrate 111 in any suitable manner (e.g., chemical adhesive, press fitting, friction, etc.).

Figure 4:
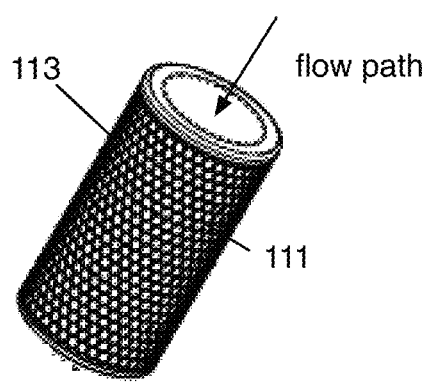
FIG. 4 depicts a variation of a substrate of an example embodiment of the air purification system.

In a first variation, the substrate 111 can be configured as a substantially cylindrical tube, as shown by example in FIG. 4, wherein a longitudinal axis of the cylindrical tube is substantially aligned with a flow path through the system 100. In a second variation, the substrate 111 can be configured as a substantially flat surface with a quadrilateral projected area normal to the direction of airflow to the substrate 111. The substrate 111 can, in variations, have a macro-geometry and a microgeometry. For example, in a first variation, the substrate 111 can have a macro-geometry corresponding to a cylinder and a micro-geometry (e.g., surface morphology) that forms a corrugated surface, a rough surface, a smooth surface, bound or loose fibers, patterned holes, and/or any other suitable micro-geometry (e.g., geometry on a smaller scale than the macro-geometry).

The macro- and/or micro-geometry can be formed in any suitable manner. In a first variation, the geometry of the substrate can be formed via stiffening agents embedded within the substrate itself (e.g., starches, stiff fibers, etc.). In a second variation, the geometry of the substrate can be enforced by an external structural member (e.g., a substantially stiff metallic mesh) coupled to the pliable substrate and thus dictating the geometric configuration of the substrate.

In a first specific example, the substrate 111 is formed in a substantially cylindrical shape having a corrugated outer surface, wherein the corrugation is along an azimuthal axis of the cylinder (e.g., undulating in the azimuthal direction). In a second specific example, the substrate 111 is formed in a substantially rectangular shape and defines a substantially smooth broad surface; in related examples, the broad surface undulates in 2 dimensions (e.g., exhibits a knurling pattern). In a third specific example, the substrate 111 has a honeycomb surface arrangement (e.g., a closely packed pattern of hexagonal three-dimensional cavities), and can be fashioned into any suitable-macro geometry (e.g., a cylinder, a cube, a sinuous layered stack, etc.). However, the substrate 111 can have any other suitable geometry.

In variations, the substrate 111 includes a textile material (e.g., felt, wool-fiber-based, synthetic-fiber-based, blended natural and synthetic fibers, etc.). However, the substrate 111 can additionally or alternatively include any other suitable fibrous material. In another variation, the substrate 111 includes a metallic surface on which nanostructures can be directly grown (e.g., via chemical vapor deposition, electrodeposition, etc.). However, the substrate 111 can additionally or alternatively include any other suitable material that can act as a medium upon which the photocatalytic material 112 can be disposed.

The substrate 111 can include both the textile material and a support structure (e.g., wire mesh, conductive material, etc.) that functions to mechanically support the textile material and can also function to give the textile material a defined shape. The shape of the support structure preferably defines the shape of the substrate 111 as discussed above; however, the support structure can additionally or alternatively have any suitable shape (e.g., in cases wherein the textile material can permanently or semi-permanently define a rigid shape without requiring an additional rigid support structure).

Figure 14A:
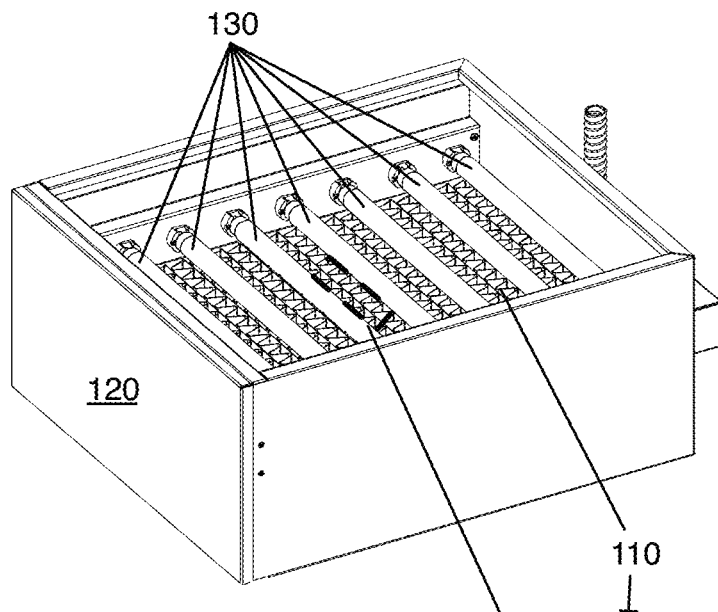
FIGS. 14A and 14B depicts a perspective view and a partial zoom view of an example embodiment of the air purification system.
Figure 14B:
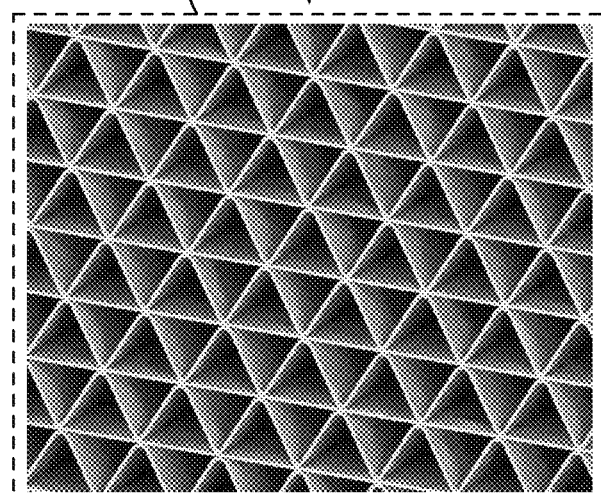

In another specific example, the photocatalytic material can be applied to a solid substrate (e.g., a foil, a slab, a wafer, etc.). The solid substrate can be formed into any suitable shape. For example, the solid substrate can be a metallic foil that is formed into a structure that includes corrugated and/or flat layers (e.g., as shown in FIG. 14). The layered structure can, in variations, be oriented to define flow pathways proximal the substrate surface (e.g., upon which photocatalytic material is disposed); for example, the flow pathways can be substantially parallel to a flow direction within a ventilation system (e.g., HVAC duct or throughway) to optimize pollutant residence time adjacent to the photocatalytic surface (e.g., without adding undue pressure loss or skin friction to the ventilation system).

The filter assembly 110 can optionally include a support structure 113 coupled to the substrate 111. The support structure functions to substantially rigidly retain the substrate 111 in a predetermined shape. The support structure can also function to enhance the conductivity and/or electron mobility of the substrate on which the photocatalytic material is disposed (e.g., in cases wherein the support structure is electrically conductive and in contact with the substrate), which can function to increase the electron-hole pair lifetime and thus the efficiency of radical creation (e.g., and resultant pollutant reduction).

In variations, the support structure can include a conductive material placed adjacent to the substrate to provide both structural support and enhanced surface conductivity. In examples, this conductive material can include a metallic mesh arranged at a surface of the substrate; the surface of the substrate can be between the substrate and the photon source but can additionally or alternatively be at an opposing side to the side illuminated by the photon source (e.g., arranged between the substrate and an innermost surface of the lumen of the housing.).

Figure 6A:
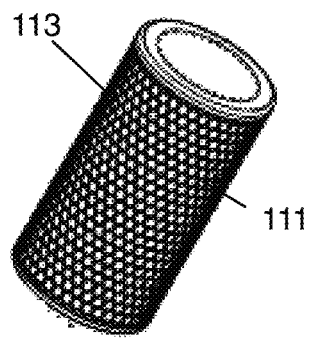
FIGS. 6A and 6B depict variations of the support structure of example embodiments of the air purification system.
Figure 6B:
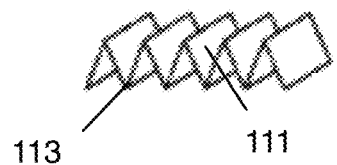

In a first variation, the support structure is an external structure in contact with the substrate. In a first example of this first variation, the support structure includes a wire mesh, and is arranged in a cylindrical tubular form factor as shown in FIG. 6A. In a second example of this first variation, the support structure defines a corrugated surface as shown in FIG. 6B. However, the support structure in this variation can be otherwise suitably arranged and/or configured.

In a second variation, the support structure is internal to the substrate. In a first example of this second variation, the support structure includes a wire mesh layer of the substrate and integrated into the substrate, that enables the substrate to be pliantly formed into any suitable shape and to hold the shape by way of the rigidity of the wire mesh layer. In a second example of this second variation, the support structure includes conductive and ductile fibers integrated into the substrate, wherein the substrate is at least partially composed of fibers that make up a fibrous media, that enables the substrate to be formed into a shape utilizing the ductility and partial stiffness of the conductive and ductile fibers (e.g., metallic fibers) integrated therein.

However, the filter assembly can, in variations, omit a support structure and/or include a support structure of any other suitable type in any other suitable configuration.

3.3 Photocatalytic Material

The photocatalytic material 112 functions to provide a catalytic site for direct and/or indirect reduction of pollutants proximal the surface of the substrate of the filter assembly 110. The photocatalytic material 112 can also function to generate an electron-hole pair upon illumination by a photon, which can generate a hydroxyl radical (or other radical) upon interacting with water vapor (or other gaseous contents) contained in the surrounding air (e.g., as part of indirect pollutant reduction). The hydroxyl radical thus generated can chemically react with reducible pollutants in the airflow to chemically reduce the pollutants and thereby eliminate the pollutants from the airflow. The electron-hole pair can also react directly with pollutants in the air (e.g., acting as a free radical), as part of direct pollutant reduction. However, the photocatalytic material 112 can provide any other suitable catalytic or reaction site.

The photocatalytic material 112 is preferably formed at least partially of nanostructures, and the nanostructures are preferably formed at least partially from one or more photocatalysts (e.g., titanium dioxide in anatase, rutile, and any other suitable phase; sodium tantalite; doped titanium dioxide, zinc oxide, any other suitable substance that catalyzes reactions in response to photon illumination, etc.), but can additionally or alternatively be formed from any other suitable material (e.g., carbon, carbon-containing compounds, etc.). The nanostructures preferably include a combination of crushed nanostructures (e.g., crushed nanotubes, crushed nanorods, crushed nanowires, etc.) and nanoparticles (e.g., spherical nanoparticles, quasi-spherical nanoparticles, oblate nanoparticles, etc.). However, the nanostructures can additionally or alternatively include uncrushed nanotubes, crushed and/or uncrushed hollow nanotubes, a homogenous or heterogeneous material made up of any of the aforementioned nanostructures and/or any other suitable nanostructures or combinations thereof in any suitable phase.

Figure 10:
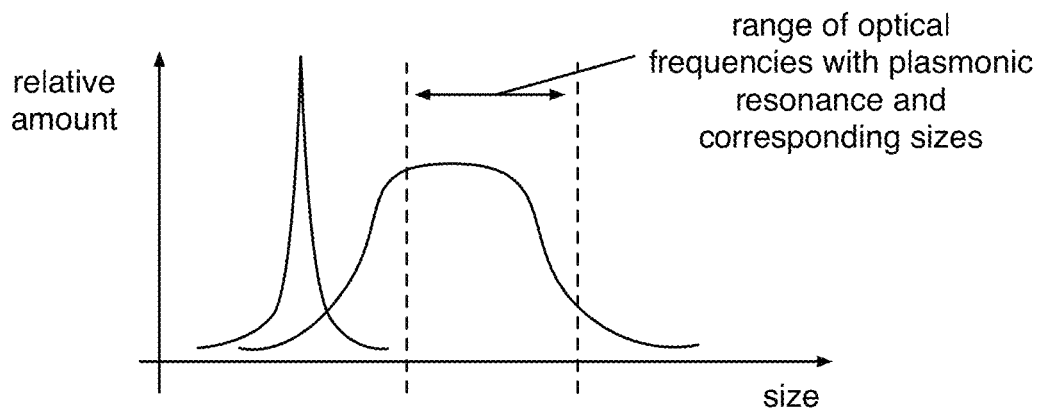
FIG. 10 depicts an example size distribution of photocatalytic material components in an example embodiment of the air purification system.
Figure 11:
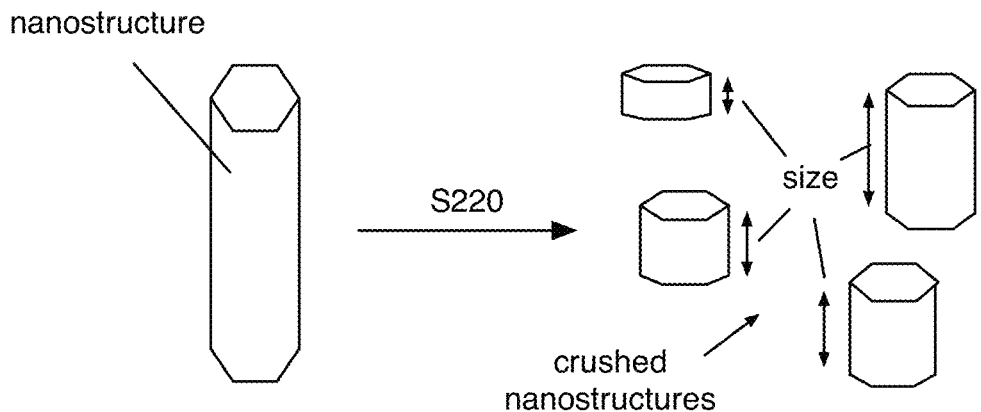
FIG. 11 depicts an example result of nanostructure crushing.

The nanostructures of the photocatalytic material 112 can function to induce plasmonic resonance with the illuminating optical frequency or frequencies. The plasmonic resonance frequency of the nanostructures of the photocatalytic material can be based on geometric properties of the nanostructures; in particular, the characteristic dimension (e.g., size) of the nanostructures can correspond to a plasmonic resonance frequency which, in cases where the resonance is excited, increases the efficiency (e.g., quantum efficiency) of the photocatalytic process and enhances PECO performance. In variations, the nanostructures can have size distributions that depend upon the nanostructure type. For example, as shown in FIG. 10, nanoparticles can have a first size distribution that is narrower than a second size distribution of crushed nanostructures. Crushing the nanostructures can result in a broader size distribution of the resulting crushed nanostructures (e.g., as compared to substantially spherical nanoparticles or nanobeads) due to the random variation in the fracture location of the nanostructures during crushing (e.g., as shown in FIG. 11). The crushed nanostructures that are added to the photocatalytic material can, in variations, be selected as a subset of a total quantity of crushed nanostructures in order to adjust the size distribution of the crushed nanostructures that are used in the system 100 (e.g., by filtering the crushed nanostructures based on size after crushing). Broadening the size distribution can increase the number of nanostructures (e.g., including both crushed nanostructures and nanoparticles) in the photocatalytic material that include a characteristic dimension that overlaps with a corresponding plasmonic resonance frequency. The nanostructures can have any suitable characteristic dimension and/or range of characteristic dimensions (e.g., 1-5 nm, 2-50 nm, 50-500 nm, etc.), which can include a characteristic diameter, characteristic length, characteristic volume, and any other suitable characteristic dimension.

The photocatalytic material 112 is preferably coupled to the substrate 111. In a first variation, the photocatalytic material 112 is secured to the fibers of a fibrous substrate 111 (e.g., by way of an adhesive, electrostatic attachment, covalent linking, polar covalent bonding, ionic bonding, Van der Waals forces, hydrogen bonds, metallic bonds, etc.). In a second variation, the photocatalytic material 112 is deposited directly onto the surface of the substrate 111 (e.g., grown on the substrate directly through chemical vapor deposition, ion deposition, etc.). The photocatalytic material 112 can be secured to a layer of the substrate 111 (e.g., a surface layer), multiple layers of the substrate 111 (e.g., a top and bottom layer), bodily attached to the substrate 111 (e.g., substantially homogenously through the volume of the substrate), or otherwise suitably secured. Additionally or alternatively, the photocatalytic material 112 can be otherwise suitably attached to the substrate 111 in any suitable manner.

Figure 5A:
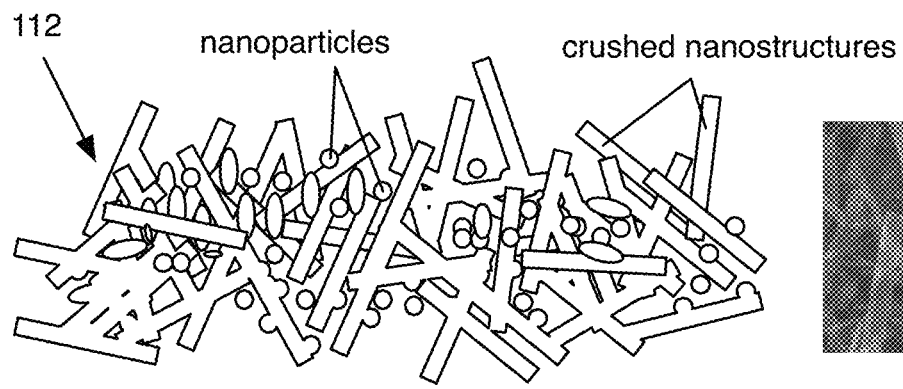
FIGS. 5A and 5B depict an example surface morphologies of an example embodiment of the photocatalytic material of the air purification system.
Figure 5B:
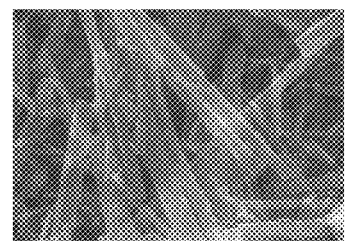

In some variations, the photocatalytic material disposed on the substrate defines an active surface area increased over an un-treated surface area of the substrate (e.g., in a hypothetical case including a substrate on which photocatalytic material is not disposed, as compared to regions of the substrate on which no photocatalytic material is disposed, etc.). In some examples, the crushed nanostructures can contribute to the active surface area by forming a porous, entangled unstructured mesh of photocatalytic material (e.g., as shown by example in FIGS. 5A and 5B).

The photocatalytic material 112 can include any suitable photocatalytic nanostructures, combined in any suitable ratio and/or combination. In variations wherein the photocatalytic material 112 includes multiple types of nanostructures, the photocatalytic material 112 can be a homogeneous mix of the multiple types of nanostructures (e.g., wherein the relative density of each nanostructure type is substantially equal at any given location on the substrate on which the photocatalytic material is disposed), a patterned combination (e.g., wherein a first set of regions of the photocatalytic material 112 disposed on the substrate 111 include substantially solely a first type or types of nanostructure, and a second set of regions include substantially solely a second type or types of nanostructure; wherein a first set of regions include photocatalytic material and a second set of regions are devoid of substantial amounts of or any photocatalytic material; etc.), or any other suitable combination. In a specific example, the photocatalytic material 112 is made up of a homogeneous combination of crushed nanorods and nanobeads, in a 1:9 ratio of the nanorods to nanobeads (e.g., 1:9 by mass, 1:9 by volume, etc.). In another example, the photocatalytic material 112 is made up of pure crushed nanorods. However, the photocatalytic material 112 can be otherwise suitably made up of any suitable combination of crushed and/or uncrushed nanostructures.

Figure 12:
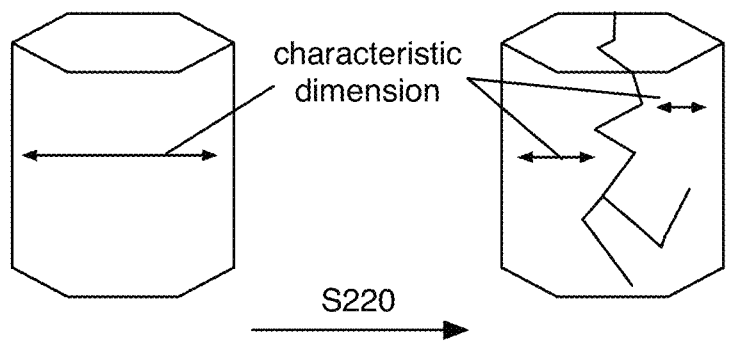
FIG. 12 depicts an example characteristic dimensional shift as the result of cracking of a nanostructure.

The crushed nanostructures (e.g., nanotubes, nanorods, etc.) of the photocatalytic material 112 can function to provide a jagged surface exposing a high spatial concentration of photocatalysis sites and/or photoreception sites (e.g., sites at which photonic energy can be absorbed and initiate photocatalysis). The crushed nanostructures and/or substrate structure (e.g., primary, secondary, tertiary, quaternary, or other structure, etc.) can also function to generate flow nonuniformities (e.g., turbulence, mixing, turbulation, etc.) that in turn promote transport of unreduced pollutants to the active region (e.g., proximal the photocatalytic material of the substrate) and/or transport of reduced pollutants (e.g., purified air components) away from the active region (e.g., away from the substrate). The crushed nanostructures can also function to present a highly active surface chemistry to pollutants (e.g., dangling bonds from previously closed-face crystal structures, disrupted crystal structure of the uncrushed nanostructure, etc.). The crushed nanostructures (e.g., in aggregate) can also function to retain pollutants proximal the photocatalytic sites (e.g., by providing nanoscale surface roughness and/or structural porosity that acts to retain pollutant molecules proximal to the surface, adsorb pollutant molecules, etc.). The resulting nanoporous surface morphology (e.g., in variants where the crushed nanostructures include hollow nanotubes and the open tubes can form nanopores, in variants where the crushed nanostructures are solid rods and multiple rods can cooperatively form nanopores based on their relative arrangement, etc.) can function to trap and/or otherwise retain pollutants proximal the photocatalytic surface, as shown by example in FIGS. 5A and 5B. The crushed nanotubes can also function to provide a reduced volumetric density of the photocatalytic material 112 and increased volumetric density of active sites (e.g., via enhanced porosity, loose packing of irregularly shaped nanostructures, etc.). The crushed nanostructures can also form cracks when crushed, and the cracks can enhance photocatalytic performance (e.g., by exposing active sites at the crack region and/or by adjusting the characteristic dimension of the crushed nanostructure to be between a free surface of the nanostructure and a crack as shown in FIG. 12).

The photocatalytic material 112 preferably includes a predetermined ratio of crushed nanotubes and spherical nanoparticles. In a first variation, the photocatalytic material 112 includes a 9:1 ratio of nanoparticles and crushed nanotubes by volume. In a related variation, the photocatalytic material 112 includes a 9:1 ratio of nanoparticles and crushed nanotubes by mass. However, the photocatalytic material 112 can include any other suitable ratio of nanoparticles (or other nanostructures) and crushed nanotubes, including the absence of either nanoparticles or crushed nanotubes, by mass and/or by volume.

In another variation, the photocatalytic material 112 includes hollow nanotubes. In a first example, the hollow nanotubes are crushed hollow nanotubes. In a second example, the hollow nanotubes are uncrushed and can be grown on the substrate 111 and/or attached to the substrate 111 without disrupting the structural integrity (e.g., crushing) of the tubes.

3.4 Photon Source

The system 100 preferably includes a photon source 130. The photon source 130 functions to illuminate the photocatalytic material 112, and thereby generate electron-hole pairs that can react with water vapor to form hydroxyl radicals. The photon source 130 can also function to generate photons at a specified photon energy or range of photon energies. The photon energies preferably correspond to at least a band gap energy of the photocatalytic material 112, such that absorption of a photon promotes an electron in the valence band of the photocatalytic material 112 to the conduction band. However, the photons generated by the photon source 130 can have any suitable range of energies. The photon source 130 can include a plurality of light emitters (e.g., light emitting diodes, fluorescent tubes, etc.), but can additionally or alternatively include any other suitable components.

The photon source 130 is preferably connected to a power source (e.g., building power, wall power, electric grid power, battery, etc.) that functions to power the photon source 130. The photon source 130 is arranged within the housing 120 such that the photons emitted therefrom illuminate the photocatalytic material 112 of the filter assembly 110. In a first variation, the photon source 130 is arranged within a void defined by the filter assembly 110 (e.g., inserted within the filter assembly) and is thus circumscribed by the filter assembly 110. In a second variation, the photon source 130 is arranged externally to the filter assembly 110 (e.g., offset therefrom, at an oblique angle to, etc.).

The photon source preferably emits optical radiation of a sufficiently low photon energy (low optical frequency, high optical wavelength) that the photons do not directly reduce pollutants (e.g., by way of direct ionization). The optical radiation can define a wavelength or frequency range of any suitable breadth in wavelength or frequency, which can depend on the photon source characteristics (e.g., a coherent photon source such as a laser can have a narrower range of emitted wavelengths than an incoherent photon source such as a light emitting diode). The optical radiation preferably defines a minimum wavelength greater than at least 280 nm (e.g., corresponding to the upper limit of UVC), and in variations can define a minimum wavelength greater than 315 nm (e.g., corresponding to the upper limit of UVB), 400 nm (e.g., corresponding to the upper limit of UVA), and any other suitable wavelength, preferably in the optical range but additionally or alternatively in any other suitable electromagnetic radiation spectral zone.

The photon source 130 can illuminate the filter assembly in various ways. In a first variation, the photon source 130 illuminates a single surface of the substrate (e.g., an inner surface of a tubular substrate configuration, an outer surface of a tubular substrate configuration, a top surface of a corrugated planar substrate configuration, etc.). In a second variation, the photon source 130 illuminates a volumetric region (e.g., via scattering and/or reflection of light) in which the substrate is arranged, thus illuminating all surfaces of the substrate. The illumination of the substrate by the photon source can, in some variations, be occluded in part by a support structure coupled to the substrate (e.g., wherein the photon source illuminates a first side of the substrate to which the support structure is also coupled). However, the photon source 130 can additionally or alternatively illuminate the substrate, and the photocatalytic material thereupon, in any other suitable manner.

The photon source 130 can include one or more components (e.g., multiple LEDs). The photon source components can be: substantially evenly distributed about the housing interior and/or about photocatalytic material 112 or filter assembly (e.g., be arranged in a grid along the housing interior, arranged in vertical, circumferential, or lateral bands along the housing interior or an insert extending through all or part of the filter assembly lumen, etc.; wherein substantial distribution can be within a manufacturing margin of error, such as less than 5%, less than 10% or any other suitable degree of error); unevenly distributed about the housing interior (e.g., housing lumen) and/or about the photocatalytic material 112 or filter assembly; arranged along the top and/or bottom of the housing interior (e.g., within a cap, in the filter attachment region); and/or arranged in any other suitable position. The photon source 130 can optionally include diffusers, splitters, lenses, or any other suitable optical component arranged within the path between the photon source (e.g., LEDs) and the illumination target (e.g., the substrate, the photocatalytic material). In one example, the optical component can diffuse and/or blend light, such that the illumination target is illuminated with a substantially homogenous illumination profile from photon point sources. In a specific example, the photon source 130 includes a plurality of light emitting diodes (LEDs) configured in a cylindrical array. The cylindrical array of LEDs is arranged within a tubular filter assembly and illuminates the internal surface of the substrate 111 of the filter assembly 110 (and the photocatalytic material disposed thereon). In related specific examples, the photon source 130 can include a plurality of LEDs arranged in array of any suitable shape (e.g., rectangular prismatic, hexagonal prismatic, conical, etc.).

The photon source can be arranged to illuminate a surface of the substrate with a substantially homogeneous illumination profile (e.g., wherein the optical illumination power is substantially the same across the surface that is illuminated, equivalent to within a relatively narrow range of optical powers such as within 1 watt, 500 milliwatts, etc.). The photon source can alternatively be arranged to illuminate a surface of the substrate with a patterned (e.g., regularly patterned) or randomly inhomogeneous (e.g., scattered, speckled, etc.) illumination profile; for example, the illumination pattern can be a checkered pattern (e.g., that is substantially aligned with a checkered pattern of photocatalytic material disposed on the substrate), a striped pattern, a kaleidoscopic pattern, and any other suitable pattern.

In variations, the photon source can be separate from the system 100 itself (e.g., the system can omit a photon source integrated therewith). For example, the photon source can include ambient light (e.g., sunlight, interior artificial lighting, exterior artificial lighting, natural lighting from any natural light source, etc.). In such variations, the system 100 can operate passively (e.g., as a painted on photocatalytic material on a building interior or exterior) or actively (e.g., with airflow urged into contact with the catalyzed surface).

3.5 Flow Control Mechanism

The system 100 can optionally include a flow control mechanism 140. The flow control mechanism 140 functions to urge fluid flow through the device (e.g., within the housing lumen between the inlet and the outlet). The flow control mechanism 140 can also function to modulate flow variables of the fluid flowing through the device (e.g., temperature, humidity, density, pressure, energy, etc.). The flow control mechanism 140 is preferably mounted to the housing 120 but can alternatively be coupled to the housing 120 from an adjacent location (e.g., as a modular attachment via a hose, tube, duct, etc.). The flow control mechanism 140 is preferably arranged proximal to at least one of the inlet and the outlet of the housing 120.

In one variation, the flow control mechanism 140 includes an impeller arranged within the housing 120, downstream of the inlet and upstream of the filter assembly 110. In another variation, the impeller is positioned downstream of the filter assembly 110. However, the impeller can be otherwise suitably arranged. In related variations, the flow control mechanism 140 can include any other suitable active flow promoter, such as a jet, a propeller, a rotor, a thermal pump, a reciprocating pump, or any other suitable mechanism for urging flow between the inlet and the outlet.

The flow control mechanism 140 is preferably arranged at a single location along the flow path through the housing 120 but can additionally or alternatively include distinct modules arranged at multiple locations along the flow path and/or adjacent to the flow path. For example, the flow control mechanism 140 can include humidity control modules distributed at plurality of locations along flow path through the housing 120, as well as plurality of pumps (e.g., impellers) positioned along the flow path (e.g., proximal to the inlet and proximal to the outlet). However, the flow control mechanism 140 can be otherwise suitable arranged or positioned.

The flow control mechanism 140 can include one or more passive flow guides. The passive flow guides function to direct airflow within the housing lumen, proximal the filter assembly 110. For example, the passive flow guides can include a set of vanes, one or more stator blades, or any other suitable structures for directing airflow. The passive flow guides are preferably defined by a portion of the interior surface of the housing 120, but can additionally or alternatively include distinct components, and/or be defined by portions of the flow control mechanism 140 (e.g., a fan cover including flow-directing slats). In a specific example, the flow control mechanism 140 includes a three-dimensional array of vanes positioned adjacent to the outlet on the downstream side thereof and are configured to generate a swirling flow action (e.g., large scale voracity) in the outlet air flow.

3.6 Controller

The system 100 can optionally include a controller 150. The controller 150 functions to control the operation of the photon source 130 between operating modes (e.g., an on mode, an off mode, etc.). The controller 150 can also function to control the operation of the flow control mechanism 140 between operating modes (e.g., an on mode, an off mode, a high-speed mode, etc.). The controller 150 is preferably communicatively coupled to the flow control mechanism 140 and the photon source 130 (e.g., via direct electrical connection, wireless data connection, a combination of data and power connections, etc.), but can additionally or alternatively be otherwise suitably coupled to any other system components. The controller 150 can, in variations, include a plurality of sensors arranged within the system 100, and can operate components between operating modes based on the sensor outputs. For example, the controller 150 can include a pollutant sensor proximal the outlet of the housing 120 (e.g., a diode laser gas sensor, a particulate sensor, etc.), and can operate the photon source 130 according to the output of the pollutant sensor (e.g., turning the photon source 130 into an on state based on detected pollutants).

Figure 7:
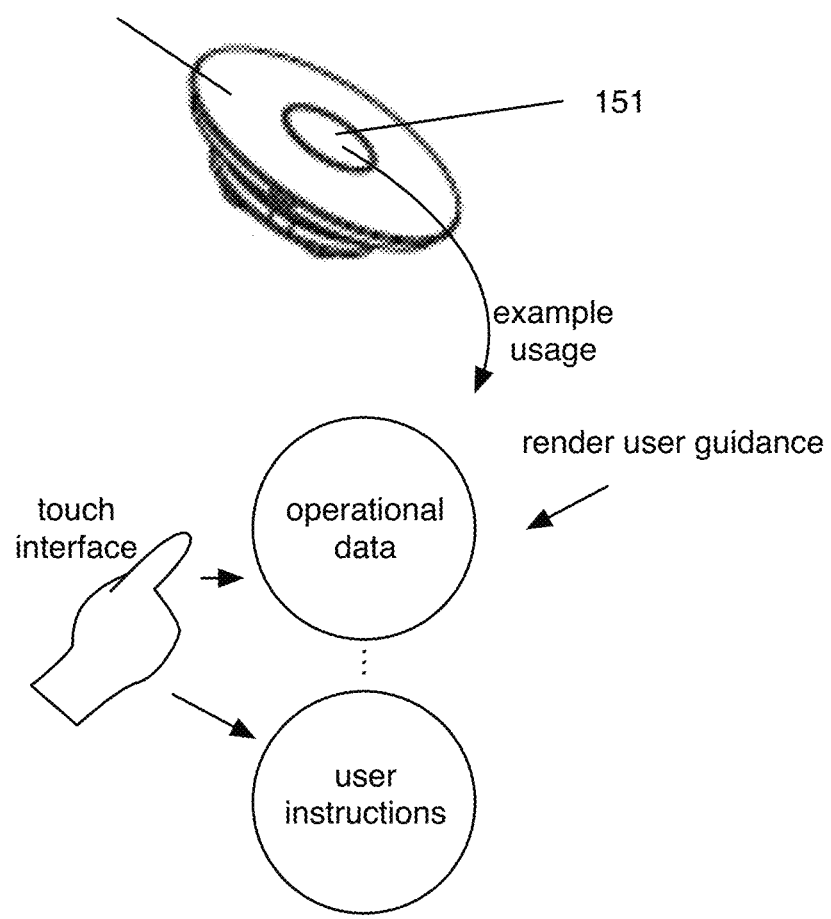
FIG. 7 depicts a user interface of an example embodiment of the air purification system.

The controller 150 can optionally include a user interface 151 that functions to enable a user to interact with the system 100 and provide user inputs to the controller 150 for the creation of control inputs to various system components. In a specific example, the user interface can include a touch screen arranged at a top portion of the external surface of the housing 120, as shown by example in FIG. 7. However, the user interface can include any other suitable interface inputs (e.g., buttons, switches, latches, keypads, microphones, wireless radios, etc.) and/or outputs (e.g., lights, speakers, wireless radios, screens, etc.).

The controller 150 can operate the system 100 between various operating modes, including a continuous mode, a closed loop mode, and a user-controlled mode. In the continuous operating mode, the system 100 is operating continuously to process and purify air. In the closed loop operating mode, the controller 150 operates the system 100 between an on state and an off state, wherein in the on state the system 100 is actively purifying air and promoting air flow through the device and in the off state the system 100 is dormant, based on sensor inputs. In the user-controlled operating mode, the system 100 is operated according to user instructions received by the controller 150. User instructions can include an operation schedule (e.g., a range of times during which the system is to be operated in the on or off states), an operation condition (e.g., a pollutant level and/or air quality metric threshold at which the system is to be activated and operated in the on state), and/or any other suitable user instructions.

3.7 Additional System Examples

A specific example of the air purification system includes a housing defining a lumen, a filter attachment region, an inlet, an outlet, and a flow pathway between the inlet and the outlet. This example also includes a filter assembly retained within the lumen intersecting the flow pathway and coupled to the filter attachment region, and the filter assembly includes a substrate (e.g., including and/or made up of a fibrous media which can be woven or nonwoven) and a photocatalytic material disposed on the substrate. In this example, the photocatalytic material is composed of a first quantity of nanoparticles (e.g., nanobeads, spheroidal nanoparticles, etc.) and a second quantity of crushed nanostructures (e.g., nanotubes, nanorods, nanowires, etc.) and the photocatalytic material is a homogenous distribution of the nanoparticles and the crushed nanostructures. The photocatalytic material in this example is composed of about one part crushed nanostructures to nine parts nanoparticles (e.g., by mass, by volume, etc.); in further examples, the photocatalytic material can be composed of a greater number of nanoparticles than crushed nanostructures (e.g., a ratio greater than one), a greater number of crushed nanostructures than nanoparticles (e.g., a ratio less than one), and any other suitable ratio of nanoparticles to crushed nanostructures. The photocatalytic material in this example can be made up at least partially of titanium dioxide in one or more phases as described above; however, any suitable photocatalyst can make up all or part of the photocatalytic material in this example. This example further includes a photon source coupled to the housing and arranged to illuminate the photocatalytic material with optical radiation defining a wavelength range that is at least partially in the visible range, and a minimum wavelength that is greater than at least the largest wavelength corresponding to UVC radiation. This example further includes a flow control mechanism coupled to the housing and arranged along the flow pathway that is operable to urge airflow along the flow pathway between the inlet and the outlet of the housing.

In this example, the crushed nanostructures can define a size distribution, which can have any suitable shape (e.g., normal or Gaussian distribution, filtered Gaussian distribution, exponential distribution, etc.). In this particular example, a peak of the size distribution can correspond to a plasmonic resonance frequency (e.g., based on an oscillation frequency corresponding to the dimension associated with size at the peak of the size distribution) that overlaps with a portion of the optical frequency range of the illuminating radiation (e.g., a peak of the optical frequency range, a tail of the optical frequency range, etc.). In a specific example, the crushed nanostructures can define a size distribution peak at a size on the order of about 50-250 nm, and the nanoparticles can define a size distribution having a peak at a size on the order of about 25 nm, wherein plasmon resonances (e.g., longitudinal or transverse surface plasmons) are excited in the crushed nanostructures and not in the nanoparticles for the optical radiation wavelength range. However, the crushed nanostructures and nanoparticles can additionally or alternatively define any suitable size distributions having any suitable size peaks.

Another specific example of the air purification system includes a filter assembly and a photon source. The filter assembly in this example includes a substrate made up at least partially of a fibrous media (e.g., woven cloth, nonwoven cloth, pressed fiber textile material, felt material, any other suitable fibrous media, etc.), and a photocatalytic material disposed on the substrate. In this example, the photocatalytic material is made up of a first quantity of crushed nanostructures (e.g., nanotubes, nanorods, nanowires, etc.). In this example, the system includes a photon source arranged to illuminate the photocatalytic material with optical radiation that defines a wavelength range having a minimum wavelength greater than 280 nanometers (e.g., corresponding to a maximum wavelength of UVC radiation).

In this example, the photocatalytic material can also be made up of a second quantity of nanoparticles (e.g., nanobeads, nanospheres, etc.); both the nanoparticles and crushed nanostructures can be at least partially made up of titanium dioxide in any suitable phase as described above. In this example, the first quantity of crushed nanostructures defines a first size distribution, the second quantity of nanoparticles defines a second size distribution, and the first size distribution is broader than the second size distribution (e.g., as shown by example in FIG. 10). In this example, a peak of at least one of the first size distribution and the second size distribution can correspond to a plasmonic resonance frequency, wherein the wavelength range of the optical radiation corresponds to an optical frequency range that overlaps the plasmonic resonance frequency; alternatively, the plasmonic resonance frequency can correspond to any suitable size within the size distribution, and the optical radiation can overlap with that portion of the size distribution to access the plasmonic resonance.

In related examples, the minimum wavelength of the wavelength range is greater than 315 nanometers (e.g., corresponding to a maximum wavelength of UVB radiation). In further related examples, the minimum wavelength of the wavelength range is greater than 400 nanometers (e.g., corresponding to a maximum wavelength of UVA radiation).

This specific example can further include a housing defining a lumen, a filter attachment region, an inlet, an outlet, and defining a flow pathway between the inlet and the outlet. In this example, the filter assembly can be arranged within the lumen along the flow pathway and coupled to the filter attachment region. In this example, the lumen defines a cylindrical shape and the housing is freestanding, and the inlet is arranged atop the housing and the outlet is at the base of the cylindrical shape (e.g., in an annular configuration). However, in related examples, the lumen can be of any suitable shape and the housing can be modular and/or configured for insertion into a larger ventilation or air purification system (e.g., not freestanding).

In this example, the system can further include a flow control mechanism coupled to the housing and arranged along the flow pathway. The flow control mechanism of this example is configured to urge airflow along the flow pathway between the inlet and the outlet of the housing (e.g., by way of pressure force, rotary force, turbine action, compressive action, vacuum action, etc.).

In another specific example, the air purification system can include a photocatalytic material made up of nanoparticles and crushed nanostructures that is applied as a mixture to a substrate (e.g., painted on, sprayed on, etc.). In this example, the photon source used with the system can be ambient light of a natural or artificial source.

However, the air purification system can additionally or alternatively be configured in any suitable manner in various examples and variations consistent with the above.

4. Method of Manufacture

Figure 8:
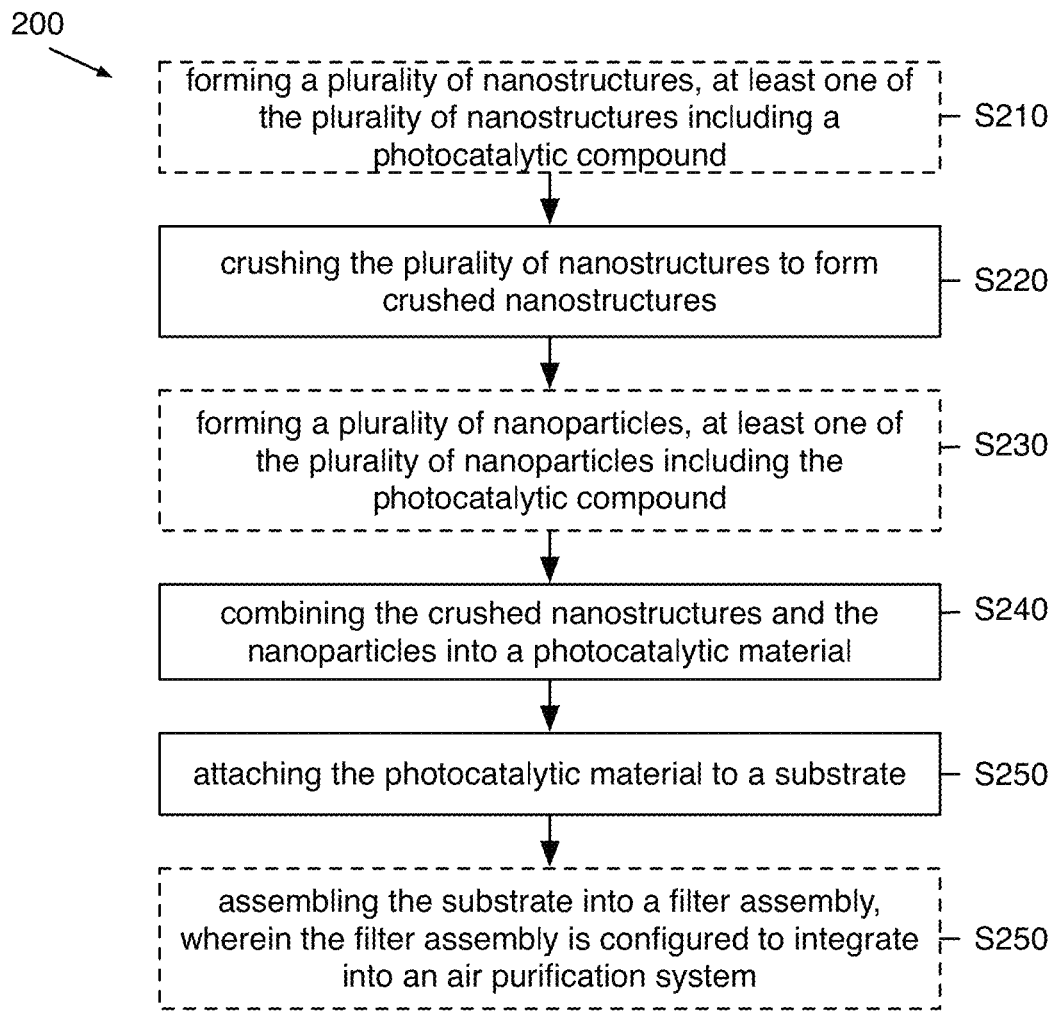
FIG. 8 depicts a flowchart of an example implementation of the method of manufacturing the air purification system.

As shown in FIG. 8, the method 200 of manufacturing an air purification system can include: forming a plurality of nanostructures (e.g., nanotubes, nanorods, nanowires, etc.), at least one of the plurality of nanostructures including a photocatalytic compound S210; crushing the plurality of nanostructures to form crushed nanostructures S220; forming a plurality of nanoparticles, at least one of the plurality of nanoparticles including a photocatalytic compound S230; combining the crushed nanostructures and the nanoparticles into a photocatalytic material S240; and attaching the photocatalytic material to a substrate S250. The method of manufacturing can also include: assembling the substrate into a filter assembly, wherein the filter assembly is configured to integrate into an air purification system S260. The method is preferably implemented to manufacture a system substantially identical to the system described above in Section 3. However, the method can be implemented to manufacture any suitable system for photocatalytic oxidation of pollutants that includes crushed photocatalytic nanotubes.

The method 200 can optionally include Block S210, which includes forming a plurality of nanostructures, at least one of the plurality of nanostructures including a photocatalytic compound. Block S210 functions to generate the nanotube structures prior to crushing the nanostructures in Block S220. The nanostructures can be hollow (e.g., nanotubes) in some variations but can be solid (e.g., nanorods) in alternative or additional variations. Block S210 can include growing the nanostructures (e.g., via a deposition process), milling the nanostructures (e.g., via an ion mill), or otherwise additively or subtractively forming the nanostructures from a material containing the photocatalytic compound. The photocatalytic compound is preferably titanium dioxide (e.g., in any suitable phase), but can additionally or alternatively be any suitable photocatalytic compound.

Figure 9:
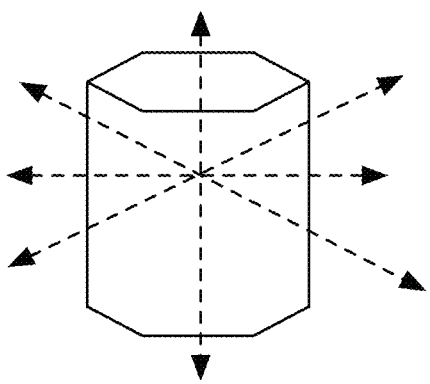
FIG. 9 depicts example cleavage planes for forming crushed nanotubes in an example implementation of the method.

Block S220 includes crushing the plurality of nanostructures to form crushed nanostructures. Block S220 functions to create the crushed nanostructures morphology (e.g., sheared nanocrystalline surfaces, nanoscale surface roughness, etc.) from the post-generation nanostructures morphology (e.g., unbroken nanotubes having a substantially smooth exterior surface). Block S220 can also function to broaden a size distribution of nanostructures by crushing them into components of various characteristic dimensions. Crushing the nanostructures can be performed using any suitable crushing process, such as anvil impact, abrasion, bombardment (e.g., particulate bombardment, sandblasting, ion impact bombardment, etc.), and any other suitable crushing technique. The nanostructures can be crushed in any suitable direction, and can generate cleavages at any suitable plane, as shown by example in FIG. 9.

Block S220 can include cracking the nanostructures and/or generating cracks in the nanostructures in the process of forming crushed nanostructures. In some variations, Block S220 can include generating predominantly cracked nanostructures in lieu of predominantly crushed nanostructures, wherein the crushed nanostructures are pulverized (e.g., crushed into multiple pieces for each original nanostructure) whereas cracked nanostructures can retain aspects of their original morphology (e.g., similar to the uncrushed nanostructure) but exhibit cracks. In such variations, Block S220 can function to enhance the photocatalytic performance of the nanostructures as described above in relation to cracking of the nanostructures.

The method 200 can optionally include Block S230, which includes forming a plurality of nanoparticles, at least one of the plurality of nanoparticles including the photocatalytic compound. Block S230 functions to generate nanoparticles for combination with the crushed nanostructures in Block S240. The nanoparticles are preferably substantially spherical and/or blob-like and can be formed through any suitable process (e.g., attrition, milling, pyrolysis, inert gas condensation, solvothermal reaction, sol-gel fabrication, structured media fabrication, etc.). However, the nanoparticles can have any other suitable form factor.

Block S240 includes combining the crushed nanostructures and the nanoparticles into a photocatalytic material. Block S240 functions to produce the photocatalytic material for attachment to the substrate in Block S250. The crushed nanostructures and nanoparticles can be combined using any suitable process or technique (e.g., vapor mixing, mechanical mixing, aqueous phase mixing and evaporative recovery, etc.), and can be combined to result in a homogeneous mixture, inhomogeneous mixture, and/or any other suitable combination.

Block S250 includes attaching the photocatalytic material to a substrate. Block S250 functions to apply the photocatalytic material produced in Blocks S210-S240 to a material that securely retains the photocatalytic material, such that the photocatalytic material can be arranged in a controllable and reusable manner within an air purification system. The photocatalytic material can be attached to the substrate in any suitable manner (e.g., adhesive, electrostatic cling, covalent linking, embedding, etc.).

The method 200 can optionally include Block S260, which includes assembling the substrate into a filter assembly, wherein the filter assembly is configured to integrate into an air purification system. Block S260 functions to prepare the amalgamated crushed nanostructures and nanoparticles, attached to the substrate, for integration into a system for air purification. The substrate can be assembled into the filter assembly in any suitable manner (e.g., integration of a wire mesh, folding, stacking, compressing, chemical adhesives, etc.).

Embodiments of the system and method and variations thereof can be embodied and/or implemented at least in part by a machine configured to receive a computer-readable medium storing computer-readable instructions. The instructions are preferably executed by computer-executable components preferably integrated with the system and one or more portions of the processor and/or the controller 150. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:
1. An air purification system comprising:
   a filter assembly comprising:
      a substrate comprising a fibrous media, and
      a photocatalytic material disposed on the substrate, wherein the photocatalytic material is comprised of a first quantity of crushed nanostructures and a second quantity of nanoparticles, wherein the crushed nanostructures consist essentially of a metal oxide photocatalyst, wherein the nanoparticles are substantially spherical; and
   a photon source arranged to illuminate the photocatalytic material with optical radiation, wherein the optical radiation defines a wavelength range comprising a minimum wavelength greater than 280 nanometers.

2. The system of claim 1, wherein the nanoparticles consist essentially of the metal oxide photocatalyst.

3. The system of claim 1, wherein the first quantity of crushed nanostructures defines a first size distribution, wherein the second quantity of nanoparticles defines a second size distribution, wherein the first size distribution is broader than the second size distribution.

4. The system of claim 3, wherein a peak of at least one of the first size distribution and the second size distribution corresponds to a plasmonic resonance frequency, wherein the wavelength range of the optical radiation corresponds to an optical frequency range that overlaps the plasmonic resonance frequency.

5. The system of claim 1, wherein the minimum wavelength of the wavelength range is greater than 315 nanometers.

6. The system of claim 5, wherein the minimum wavelength of the wavelength range is greater than 400 nanometers.

7. The system of claim 1, further comprising a housing comprising a lumen, a filter attachment region, an inlet, an outlet, and defining a flow pathway between the inlet and the outlet, wherein the filter assembly is arranged within the lumen along the flow pathway and coupled to the filter attachment region.

8. The system of claim 7, wherein the lumen defines a cylindrical shape, wherein the housing is freestanding, wherein the inlet is arranged atop the housing and the outlet is arranged proximal a base of the cylindrical shape.

9. The system of claim 7, further comprising a flow control mechanism coupled to the housing and arranged along the flow pathway, wherein the flow control mechanism is configured to urge airflow along the flow pathway between the inlet and the outlet of the housing.

10. The system of claim 2, wherein the metal oxide photocatalyst comprises titanium dioxide.

11. The system of claim 1 wherein the ratio of the first quantity of the crushed nanostructures to the second quantity of nanoparticles by mass is 1 to 9.

12. The air purification system of claim 3, wherein a peak of the first size distribution is between about 50-250 nm, and wherein a peak of the second size distribution is about 25 nm.

* * * * *